United States Patent [19]

Bohm et al.

[11] 4,088,643

[45] May 9, 1978

[54] PROCESS FOR THE PRODUCTION OF AZODICARBONAMIDE

[75] Inventors: Siegfried Böhm; Karlfried Wedemeyer, both of Cologne, Germany

[73] Assignee: Bayer Aktiengesellschaft, Leverkusen, Germany

[21] Appl. No.: 731,477

[22] Filed: Oct. 12, 1976

[30] Foreign Application Priority Data

Oct. 30, 1975 Germany .............................. 2548592

[51] Int. Cl.$^2$ ...................... C07C 107/02; C01B 7/00
[52] U.S. Cl. .................................. 260/192; 423/500; 423/502; 423/503
[58] Field of Search ......................................... 260/192

[56] References Cited

U.S. PATENT DOCUMENTS 3,190,873  6/1965  Porter .................................. 260/192
3,366,622  1/1968  Challinor et al. .................... 260/192

FOREIGN PATENT DOCUMENTS 47-7,005  2/1972  Japan .................................. 260/192

OTHER PUBLICATIONS

Okuse et al. (I), Chemical Abstracts, vol. 73, #125895h, (1973).

Okuse et al. (II), Chemical Abstracts, vol. 73, #65826, (1973).

*Primary Examiner*—Floyd D. Higel
*Attorney, Agent, or Firm*—Burgess, Dinklage & Sprung

[57] ABSTRACT

A process for the preparation of azodicarbonamide by oxidation of hydrazodicarbonamide in an aqueous suspension containing hydrogen peroxide wherein the reaction is carried out in the presence of iodine at a temperature between 50° and 95° C while the reaction mixture has a pH ranging from 1.0 to 5.0.

14 Claims, No Drawings

PROCESS FOR THE PRODUCTION OF AZODICARBONAMIDE

BACKGROUND OF THE INVENTION

FIELD OF THE INVENTION

The invention relates to a process for the preparation of azodicarbonamide by oxidation of hydrazodicarbonamide with hydrogen peroxide.

DISCUSSION OF THE PRIOR ART

Azodicarbonamide is a known foaming agent for the production of mouldings which have a porous or sponge-like structure (German Patent Specification 871,835). It can be obtained both by electrolytic oxidation and by chemical oxidation of hydrazodicarbonamide (DT-OS (German Published Specification No.) 2,016,764 and DT-OS (German Published Specification No.) 2,341,928).

According to JA-AS (Japanese Published Specification) 6,166/67, oxidation with hydrogen peroxide in the presence of hydrobromic acid or its salts is particularly advantageous since, in accordance with the equation

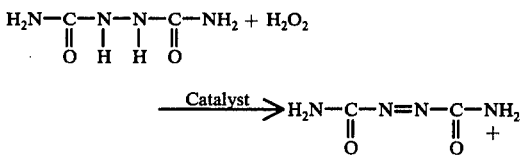

only water is formed as a by-product and it is said that the amount and degree of acidity of the resulting waste water are also less than in the case of the processes of the state of the art (compare DT-OS (German Published Specification No.) 2,341,928, page 3, 2nd paragraph).

However, when the oxidation with hydrogen peroxide is carried out in the presence of a bromine compound, it is also necessary for an acid which has a strength at least equal to that of acetic acid to be present (DT-OS (German Published Specification No.) 2,341,928, page 6, final paragraph) and this is used in a concentration of 5 to 45% by weight, and preferably of 10 to 40% by weight in the case of sulphuric acid. Therefore, the use of hydrogen peroxide as the oxidising agent also leads to an acid mother liquor being obtained and the elimination of this poses problems in respect of the load on the effluent and of environmental protection, apart from the fact that the acid, which is used merely as an auxiliary for the oxidation, is lost.

Thus, the problem of finding a process for the oxidation of hydrazodicarbonamide to azodicarbonamide which does not pollute the environment and in which, as far as possible, no auxiliaries, or only very small amounts of auxiliaries, are used has not yet been solved hitherto, even by the use of hydrogen peroxide as the oxidising agent.

SUMMARY OF THE INVENTION

It has now been found that hydrazodicarbonamide can be oxidised in aqueous suspension with hydrogen peroxide to give azodicarbonamide in a particularly advantageous manner when the reaction is carried out in the presence of iodine at temperatures of between 50° and 95° C and in the pH range between 1.0 and 5.0.

Hydrazodicarbonamide and its preparation are known (German Patent Specification No. 945,235, DT-OS (German Published Specification No.) 2,057,979 and DT-OS (German Published Specification No.) 2,210,317).

Iodine is used in an amount of 0.01 to 0.3% by weight, and preferably 0.04 to 0.08% by weight, relative to the hydrazodicarbonamide employed.

The amount of iodine which is used in the process according to the invention can also depend on the amount of hydrazodicarbonamide which is employed. If only a small amount of hydrazodicarbonamide is oxidised and if the reaction volume is small, the possibility that iodine will vaporise from the reaction mixture and that its concentration will fall very rapidly is generally greater than when, with a large amount of hydrazodicarbonamide, a correspondingly large amount of iodine is also employed in the same concentration ratio. Therefore, it is generally appropriate, when the amounts reacted are small, to keep to the upper region of the concentration range indicated for iodine, whilst in the case of larger batches it can also be advantageous to employ lower concentrations of iodine.

In place of iodine one can also use compounds which contain iodine and which supply iodine under the reaction conditions. Compounds which can be used are, in particular, hydriodic acid and its water-soluble salts; appropriately, readily accessible salts are chosen, for example alkali metal iodides and alkaline earth metal iodides, in particular lithium iodide, sodium iodide and potassium iodide. If compounds containing iodine are used in place of iodine, the amount employed is, of course, that which is equivalent to the amount of iodine to be used.

In general, the process according to the invention is appropriately carried out in the temperature range between 60° and 90° C. It is possible for the temperature to fall below or to exceed the stated temperature but in general this is not appropriate since the rate of reaction decreases as the temperature falls and at a higher temperature substances start to be lost due to thermal decomposition and, furthermore, the acid consumption increases.

The reaction is preferably carried out in the temperature range between 70°, and especially 75°, and 85° C.

In general, the process according to the invention is carried out at a pH value of the aqueous suspension of between 1.5 and 5.0. The reaction is preferably carried out in the pH range of 2.0 to 4.0.

However, the pH values can also fall below or exceed the abovementioned values. However, this is generally not appropriate since, at lower pH values, the rate of reaction becomes lower and the acid consumption, in order to maintain the pH values becomes greater and because, at higher pH values, the ease with which hydrogen peroxide undergoes thermal decomposition becomes greater and the catalytic action of the iodine is reduced.

However, one can compensate for the choice of a less favourable pH value by prolonging the reaction time and/or by a higher catalyst concentration.

In general, it is not important which acid is used to adjust the pH. In principle, all acids of adequate strength can be used. However, the acid chosen will, of course, be an acid which is readily accessible, which does not react with hydrogen peroxide and which has an anion which poses as few effluent problems as possible. In particular, hydrochloric acid, phosphoric acid and, preferably, sulphuric acid can be used.

The concentration of the acid used is not an important factor. Appropriately, the acid is used in the customary concentration. However, it can be advantageous to choose as high as possible a concentration in order to avoid an unnecessary increase in the volume of the reaction solution.

The amount of acid used depends on the given conditions in a particular case since, as has been stated, the acid is required only to adjust the pH. In general, when sulphuric acid is used, about 0.7 to 3.0% by weight, relative to the hydrazodicarbonamide employed, are necessary.

Hydrogen peroxide can be employed both in the pure form and as an aqueous solution. Appropriately, the commercially available 30 to 70% strength by weight concentrates are used since the concentration of hydrogen peroxide in the reaction mixture is not of fundamental importance.

In general, it is appropriate to use $H_2O_2$ in excess of the stoichiometrically required amount of one mol per mol of hydrazodicarbonamide. Advantageously, the excess is 5 to 25 mol % of $H_2O_2$.

Although the azodicarbonamide formed is not attacked by $H_2O_2$, reactions of impurities in the hydrazodicarbonamide employed and products of the thermal decomposition of small amounts of the azodicarbonamide formed, as well as the decomposition of $H_2O_2$, can, however, give rise to a consumption of $H_2O_2$ which exceeds the stoichiometrically required amount, so that the use of an excess of $H_2O_2$ is advantageous. The amount of this excess which is appropriately to be employed will depend on the given conditions in the particular case and it will be possible to determine this easily by a few experiments. As already mentioned, too high an excess is not harmful but is unnecessary.

In general, the process according to the invention is carried out as follows.

Hydrazodicarbonamide is suspended in water and iodine or the chosen compound containing iodine which supplies iodine under the reaction conditions, is added, the suspension is heated to the chosen reaction temperature and, after the pH value has been adjusted, hydrogen peroxide is added and, during the addition, the said pH value is maintained by adding further acid.

The amount of water used to prepare the aqueous suspension is not important. Of course, sufficient water is used to obtain a stirrable suspension, so that homogeneous distribution of the hydrogen peroxide, which is added, in the reaction mixture can be achieved by stirring. In general, a weight ratio of hydrazodicarbonamide:water of about 1:1 has proved advantageous. However, one can also use a smaller or greater amount of water but an increase in the amount of water needlessly requires greater reaction volumes and amounts of heat for the same conversion.

Iodine, or the chosen compound containing iodine, can be added at room temperature prior to heating or only at the reaction temperature.

The pH value can be adjusted immediately after the iodine or the compound containing iodine has been added. In general, a small amount of acid is required for this, as has already been mentioned above.

In the case where hydriodic acid or another acid iodine compound has been chosen as the compound containing iodine and the pH value of the aqueous suspension is below 1.5, or the intended pH value, one can either adjust the pH to the desired higher value by adding a corresponding amount of an alkaline solution, preferably an alkali metal hydroxide solution, especially sodium hydroxide solution or potassium hydroxide solution, until the desired value is reached or wait for the pH value or rise to the desired value during the oxidation and then maintain the pH value at the desired value by adding acid. In fact, in general, the pH value of the reaction mixture rises during the reaction due to the formation of small amounts of impurities which have a basic reaction.

Since the reaction is exothermic it is generally not necessary to supply further heat after heating to the reaction temperature and the reaction temperature can be maintained by appropriate control of the addition of hydrogen peroxide. However, it can also be advantageous to remove the resulting heat of reaction by cooling and to add hydrogen peroxide correspondingly more rapidly.

Iodine can vaporise at the reaction temperature and is appropriately collected in an absorption solution which reduces it to iodide. Absorption solutions of this type are known; an aqueous solution of sodium pyrosulphite ($Na_2S_2O_5$) is advantageously used.

When the reaction has ended, the azodicarbonamide formed can be separated off from the mother liquor in the customary manner, for example by filtration.

The iodine contained in the mother liquor can be driven out, if necessary after adding further hydrogen peroxide in order to oxidise iodide, by means of steam or a stream of gas, for example air or nitrogen, and recovered. One can also heat the mother liquor to the boil, in which case the iodine passes over with steam.

One can, of course, transfer all of the iodine contained in the mother liquor into the abovementioned absorption solution and re-use the iodine solution, thus obtained, for oxidation of an equal amount of hydrazodicarbonamide, so that the same amount of iodine theoretically can be used to oxidise unlimited amounts of hydrazodicarbonamide.

Excess $H_2O_2$ contained in the mother liquor already decomposes when the mother liquor is heated in order to drive out the iodine or can be decomposed, after neutralising the mother liquor, by boiling.

After the iodine has been driven off and the $H_2O_2$ has been decomposed, the mother liquor contains, in addition to small amounts of organic impurities which were contained in the hydrazodicarbonamide or have been formed by thermal decomposition of azodicarbonamide, only the anions of the acid used in order to adjust the pH, preferably sulphate. The amount is generally about one % by weight, relative to the hydrazodicarbonamide employed.

The iodine employed can be recovered particularly advantageously as follows and, at the same time, the mother liquor can also be re-used.

The absorption solution, in which the iodine which vaporises during the reaction has been collected and which contains, in a sufficient amount, the reducing agent required to reduce iodine to iodide, is added to the mother liquor and, thus, all of the iodine contained in the mother liquor is reduced to iodide, if necessary water is distilled off until the original volume of the mother liquor or the volume of the amount of water used to prepare the aqueous suspension of hydrazodicarbonamide has been reached and this solution is used in place of water to prepare the aqueous suspension of hydrazodicarbonamide. In this way, fresh water can also be saved. It is true that the salt content of the mother liquor increases every time it has been re-used.

However, the advantage of the saving of fresh water can outweigh the disadvantage of the higher salt content in the effluent.

In particular, the recovery, which has been described above, of the iodine employed and of the mother liquor can be advantageous for continuous operation of the process according to the invention. In order to prevent the salt content of the aqueous solution rising too high one can, for example, continuously withdraw from the system that amount of the total volume, which is finally obtained, of mother liquor, washing water and absorption solution which is in excess of the original volume of the amount of water used.

As already mentioned, the particular advantage of the process according to the invention is that the auxiliaries consumed are only small amounts of an acid, preferably sulphuric acid, in order to maintain the pH range during the reaction, and of a reducing agent for iodine, preferably sodium pyrosulphite, and that, accordingly, only small amounts of salts, preferably sulphates, are contained in the mother liquor. The extent to which the process pollutes the environment is thus particularly small.

A further advantage of the process according to the invention, that is to say the quantitative recovery of the iodine, has already been mentioned. Furthermore, in order to carry out the process according to the invention it is not necessary to isolate the hydrazodicarbonamide after it has been prepared. If, for example, hydrazodicarbonamide is prepared from urea and hydrazine or hydrazine hydrate at elevated temperature and under elevated pressure by reacting urea with hydrazine or hydrazine hydrate in an aqueous medium at 105° to 140° C and under a pressure of 1.2 to 3.8 bars, the reaction product can be employed direct, without isolation and purification of the resulting hydrazodicarbonamide, as an aqueous suspension of the hydrazodicarbonamide in accordance with the process of the invention. It is true that, in this case, because the suspension may contain excess urea or hydrazine hydrate, ammonium salts and other oxidisable impurities, a higher consumption of $H_2O_2$ is to be expected and, thus, a larger excess is necessary than when hydrazodicarbonamide is employed in a fresh water suspension, but this disadvantage can be more than compensated by the operations which are dispensed with. In contrast to the oxidation with chlorine, which is carried out industrially, the formation of explosive nitrogen-halogen compounds is not to be expected with the small amount of iodine which is used.

EXAMPLE 1

900 g (7.63 mols) of hydrazodicarbonamide are suspended in 1,000 ml of water and 1.25 g of 57% strength by weight hydriodic acid are added. Whilst stirring vigorously, the suspension is warmed to about 80° C and the pH value is adjusted to 3.0 by the dropwise addition of 10% strength by weight sodium hydroxide solution. 546 g of 50% strength by weight hydrogen peroxide (7.98 mols of $H_2O_2$) are then added in the course of about 4 hours. By regulating the addition of hydrogen peroxide, the reaction temperature is kept between about 78° and 85° C without supplying heat and the temperature is prevented from rising above 85° C, if necessary by means of external cooling. At the same time, the pH value of the suspension is controlled and kept at about 3.0 by adding 12% strength by weight sulphuric acid. The pH should not fall outside the range of 2.5 to 3.5.

During the oxidation, small amounts of iodine sublime and these are passed through a tube, which has been warmed to about 80° C, into an absorption vessel which contains a solution of 0.4 g of $Na_2S_2O_5$ in 60 ml of $H_2O$.

After all of the hydrogen peroxide has been added dropwise, the mixture is stirred for about a further 2 hours at the reaction temperature, during which time the pH value is maintained, as described above. A total of about 49 g of 12% strength by weight $H_2SO_4$ are consumed.

The reaction product is then filtered off, washed with 200 ml of water and dried. In this way 875 g (98.8% of theory) of azodicarbonamide which has a melting point of 230° C (decomposition) are obtained.

5 g of 50% strength by weight hydrogen peroxide are added to the filtrate and the washing water and the mixture is heated to the boil, the distillate being collected in the abovementioned absorption solution. In the course of about 15 minutes, the iodine from the mother liquor, together with about 60 ml of water, has distilled over quantitatively and been reduced. The absorption solution can be added to a new batch in place of iodine.

The mother liquor is then neutralised at about 90° C and kept at this temperature for about 45 minutes in order to decompose excess $H_2O_2$. The mother liquor contains about 9 g of salts, corresponding to one % by weight, relative to the hydrazodicarbonamide employed.

The total consumption of $H_2SO_4$ is about 6.1 g, which corresponds to about 0.7% by weight or 0.8 mol %, relative to the hydrazodicarbonamide employed.

EXAMPLES 2-6

The amount of hydrazodicarbonamide indicated in Table I which follows was suspended in the indicated volume of water and 1.25 g of 57% strength by weight hydriodic acid were added. Whilst stirring vigorously, the suspension is warmed to approximately the temperature indicated in Table I and the pH value is adjusted to 3.0 by the dropwise addition of 10% strength by weight sodium hydroxide solution. 105 mol % of the stoichiometrically required amount of 50% strength by weight hydrogen peroxide are then added in the course of the indicated reaction time. Without supplying heat, the reaction temperature is kept, on average, at about the indicated temperature by regulating the addition of hydrogen peroxide and the temperature is prevented from exceeding the indicated temperature by more than 5° C, if necessary by means of external cooling. At the same time, the pH value of the suspension is controlled, and kept at about 3.0, as described in Example 1.

Subsequently, as described in Example 1, the reaction product is filtered off, washed and dried and its azodicarbonamide content is determined by analysis. The yield of azodicarbonamide which is determined in this way is given in % of theory in Table I which follows.

Table I

| Example No. | Hydrazodi-carbonamide g | Water ml | Reaction temperature °C | Reaction time hours | Mol % of HI, relative to hydrazo-dicarbonamide | Yield of azodicarbon-amide, % of theory |
|---|---|---|---|---|---|---|
| 2*a | 225 | 500 | 50 | 10 | 1.6* | 84 |
| b | 225 | 1,000 | 50 | 12 | 1.6* | 94 |
| 3 | 225 | 500 | 60 | 8 | 0.32 | 93 |
| 4 | 450 | 500 | 70 | 8 | 0.16 | 95 |
| 5 | 900 | 1,000 | 90 | 6 | 0.08 | 94 |
| 6 | 450 | 500 | 95 | 5 | 0.16 | 89 |

*Note:
In contrast to the general description given above, 6.25 g of 57% strength by weight hydriodic acid were used in Example 2, in place of 1.25 g.

EXAMPLES 7 and 8

450 g of hydrazodicarbonamide were suspended in 500 ml of water in each case and 1.25 g of 57% strength by weight hydriodic acid were added. Whilst stirring vigorously, the suspension is warmed to approximately the temperature indicated in Table II and the pH value is adjusted to 4.0 by the dropwise addition of 10% strength by weight sodium hydroxide solution. The amount of 32% strength by weight hydrogen peroxide which corresponds to 115 mol % of the stoichiometrically required amount of $H_2O_2$ is then added in the course of the indicated reaction time.

The reaction temperature is kept at, on average, approximately the indicated temperature by supplying heat. At the same time, the pH value of the suspension is controlled, as described in Example 1, and kept at about 4.0.

Subsequently, as described in Example 1, the reaction product is filtered off, washed and dried and its azodicarbonamide content is determined by analysis. The yield, determined in this way, of azodicarbonamide is given in % of theory in Table II which follows.

Table II

| Ex. No. | Reaction temperature °C | Reaction time (hours) | Mol % of HI, relative to hydrazodi-carbonamide | Yield of azodi-carbonamide, % of theory |
|---|---|---|---|---|
| 7 | 60 | 12 | 0.16 | 99 |
| 8 | 70 | 12 | 0.16 | 98 |

EXAMPLES 9 to 12

The amount of hydrazodicarbonamide indicated in Table III which follows was suspended in the indicated amount of water and 1.25 g of 57% strength by weight hydriodic acid were added. Whilst stirring continuously, the suspension was warmed to about 80° C and the pH value was adjusted, by the dropwise addition of 10% strength by weight sodium hydroxide solution, to the value indicated in Table III. Subsequently, 105 mol % of the stoichiometrically required amount of 50% strength by weight $H_2O_2$ were added in the course of the indicated reaction time and, without supplying heat, the reaction temperature was kept at about 80° C by regulating the addition of hydrogen peroxide, as described in Example 1; in Example 12 only, 120 mol % of the stoichiometrically required amount of $H_2O_2$ were added. At the same time, the pH value of the suspension was controlled and, in the manner described in Example 1, kept at the value indicated in Table III.

Table III

| Example No. | Hydrazodi-carbonamide g | Water ml | Reaction time hours | pH | Mol % of HI, relative to hydrazo-dicarbonamide | Yield of azodicarbon-amide, % of theory |
|---|---|---|---|---|---|---|
| 9 | 450 | 500 | 6 | 1.5 | 0.16 | 97 |
| 10 | 450 | 500 | 5 | 2.0 | 0.16 | 96.5 |
| 11 | 450 | 500 | 5 | 4.0 | 0.16 | 95.5 |
| 12 | 450 | 500 | 5 | 4.5 | 0.16 | 95.5 |

EXAMPLE 13

225 g (1.91 mols) of hydrazodicarbonamide are suspended in 500 ml of water and 1.25 g of 57% strength by weight hydriodic acid (0.32 mol % of HI, relative to hydrazodicarbonamide) are added. Whilst stirring vigorously, the suspension is warmed to about 80° C and the pH value is adjusted to 3.0 by the dropwise addition of 10% strength by weight sodium hydroxide solution. Subsequently, 137 g of 50% strength by weight hydrogen peroxide are added in the course of about 3 hours, the reaction temperature being kept at about 80° C and the pH value being kept at 3.0 in the same manner as has been described in Example 1. The reaction mixture is then worked up in the same way as has been described in Example 1. 215 g (96.5% of theory) of azodicarbonamide are obtained.

EXAMPLE 14

900 g of hydrazodicarbonamide are suspended in 1,000 ml of water and 0.45 g of sodium iodide (0.04 mol %, relative to hydrazodicarbonamide) are added. Whilst stirring vigorously, the suspension is warmed to about 90° C and the pH value is adjusted to 3.0 by the dropwise addition of 10% strength by weight sodium hydroxide solution. In the same manner as described in Example 1, 575 g of 50% strength by weight hydrogen peroxide (8.35 mols of $H_2O_2$) are added in the course of 6 hours. The reaction temperature is kept at 90° C and the pH value is kept at 3.0 in the same way as has been described in Example 1. The reaction mixture is then stirred for a further 1 hour and cooled to about 80° C and 5 g of 50% strength by weight $H_2O_2$ are added. Subsequently, 100 l of air are blown in one hour from a submerged frit through the warm suspension which is at 80° C. The stream of air containing iodine is passed through an ice-cooled washing bottle filled with a solution of 0.4 g of sodium pyrosulphite in 60 ml of water and in this bottle the iodine is absorbed and reduced to sodium iodide.

The reaction mixture is then cooled to about 50° C and the reaction product is filtered off. 841 g (95% of theory) of azodicarbonamide are obtained.

The mother liquor does not contain either iodine or iodide ions. The iodine employed has been removed quantitatively from the mother liquor.

EXAMPLE 15

450 g (3.81 mols) of hydrazodicarbonamide are suspended in 500 ml of water and 1.25 g of 57% strength by weight hydriodic acid (0.16 mol % of HI, relative to hydrazodicarbonamide) are added. Whilst stirring vigorously, the suspension is warmed to about 80° C and the pH value is adjusted to 3.0 by the dropwise addition of 10% strength by weight sodium hydroxide solution. 280 g of 50% strength by weight hydrogen peroxide (4.11 mols of $H_2O_2$) are then added in the course of about 4 hours. The reaction temperature is kept at about 80° C and the pH value is kept at about 3.0, as described in Example 1.

After all of the hydrogen peroxide has been added dropwise, the mixture is stirred for a further 1 hour at the reaction temperature, the pH value is then adjusted to 4.0 with 10% strength by weight sodium hydroxide solution and, without further pH control, the mixture is stirred for a further hour at about 80° C. The reaction product is then filtered off, washed, rinsed with 100 ml of water and dried. 432 g (97% of theory) of azodicarbonamide are obtained.

The mother liquor from which the reaction product has been filtered off, the washing water and the $Na_2S_2O_5$ solution, in which the iodine which sublimes has been collected, as described in Example 1, are combined and concentrated to the original volume of 500 ml by distillation. The resulting distillate is salt-free and iodine-free.

EXAMPLE 16

450 g of hydrazodicarbonamide are suspended in the concentrated mother liquor obtained according to Example 15 and oxidised, whilst stirring vigorously, at 80° C and at a pH value of 3.0, in the course of 4 hours with 280 g of 50% strength by weight hydrogen peroxide, as described in Example 15.

437 g (98.5% of theory) of azodicarbonamide are obtained.

Example 17

(a) 1,634 g (27.5 mols) of urea, 649 g (13 mols) of 100% strength hydrazine hydrate and 980 ml of water are heated, in a 10 l steel autoclave, to about 120° C, whilst stirring well. The pressure is allowed to rise up to 2.0 bars and is then adjusted to 1.2 bars by means of a reducing valve. The aqueous ammonia which distils off is condensed in a steel condenser and collected in a measuring vessel. The amount of water in the autoclave is kept approximately constant by pumping in fresh water. The reaction has ended after 7 hours. A total of about 4.5 l of water are distilled off. The hydrazodicarbonamide which has precipitated is filtered off and dried; 1,475 g (96.5% of theory, relative to the hydrazine hydrate employed) of hydrazodicarbonamide are obtained. The mother liquor has a volume of 1.4 l and is diluted to 1.6 l.

(b) 1.25 g of 57% strength by weight hydriodic acid are added to 900 g of the hydrazodicarbonamide obtained according to (a) and 1,000 ml of the mother liquor from (a) and the mixture is warmed to about 80° C, whilst stirring vigorously. The pH value is adjusted to 3.0 as described in Example 1 and, as described in Example 1, is kept at this value during the reaction. Whilst maintaining a reaction temperature of about 80° C, as described in Example 1, 600 g of 50% strength by weight hydrogen peroxide (8.77 mols of $H_2O_2$) are added in the course of about 4 hours. Initially a vigorous evolution of nitrogen and carbon dioxide takes place and has to be controlled by intensive stirring and appropriate regulation of the addition of $H_2O_2$, in order to prevent the suspension foaming over.

Subsequently, the mixture is stirred for a further 2 hours at about 80° C whilst maintaining a pH value of 3.0 and the reaction product is then filtered off, washed with 200 ml of water and dried. In this way, 873 g (98.5% of theory) of azodicarbonamide are obtained.

As is shown by the evolution of nitrogen and carbon dioxide at the start of the oxidation with $H_2O_2$, the mother liquor from the preparation of hydrazodicarbonamide contains impurities which can be oxidised more easily than hydrazodicarbonamide. A larger excess of $H_2O_2$ than in Example 1 has therefore also been used. In the same way, a larger amount of $H_2SO_4$ is required in order to maintain the pH value of 3.0; 26 g of concentrated sulphuric acid were consumed, which corresponds to about 3% by weight of $H_2SO_4$, relative to the amount of hydrazodicarbonamide employed.

What is claimed is:

1. In a process for the preparation of azodicarbonamide by oxidation of hydrazodicarbonamide in an aqueous solution with hydrogen peroxide, the improvement which comprises carrying out the process in the presence of iodine at a temperature of between 50° and 95° C while the reaction mixture is maintained at a pH in the range of from 1.0 to 5.0.

2. A process according to claim 1 wherein the iodine which is present in the reaction mixture is supplied by an iodine containing compound which compound supplies iodine under the reaction conditions prevailing.

3. A process according to claim 1 wherein hydroiodic acid or a water soluble salt thereof is employed as the source of iodine.

4. A process according to claim 1 wherein the iodine concentration of the reaction mixture is 0.01 to 0.3 percent by weight iodine based upon the weight of hydrazodicarbonamide.

5. A process according to claim 4 wherein the amount of iodine is 0.04 to 0.08 weight percent based upon the weight of hydrazodicarbonamide.

6. A process according to claim 1 wherein the reaction is carried out at a temperature of between 60° and 90° C.

7. A process according to claim 6 wherein the reaction is carried out at a temperature of between 70° and 85° C.

8. A process according to claim 7 wherein the reaction is carried out at a temperature of between 75° and 85° C.

9. A process according to claim 1 wherein the reaction is effected at a pH of between 1.5 and 5.0.

10. A process according to claim 9 wherein the reaction is effected at a pH of between 2.0 and 4.0.

11. A process according to claim 1 wherein the pH is adjusted by the addition of hydrochloric acid, phosphoric acid or sulfuric acid.

12. A process according to claim 1 wherein 1.05 to 1.25 mols hydrogen peroxide are employed per mol of hydrazodicarbonamide.

13. A process according to claim 1 wherein the reaction is carried out in a reaction mixture consisting essentially of said hydrazodicarbonamide, water, hydrogen peroxide and iodine.

14. A process according to claim 13 wherein the reaction is carried out at a temperature between 70° and 85° C.

* * * * *